(12) United States Patent
Nedic

(10) Patent No.: US 7,340,961 B2
(45) Date of Patent: Mar. 11, 2008

(54) FIXTURE AND METHOD FOR MEASURING ELONGATION

(75) Inventor: Cedo Nedic, Ann Arbor, MI (US)

(73) Assignee: Hayes Lemmerz International, Inc., Northville, MI (US)

( * ) Notice: Subject to any disclaimer, the term of this patent is extended or adjusted under 35 U.S.C. 154(b) by 126 days.

(21) Appl. No.: 11/196,854

(22) Filed: Aug. 4, 2005

(65) Prior Publication Data

US 2007/0028701 A1    Feb. 8, 2007

(51) Int. Cl.
    *G01N 3/02* (2006.01)
(52) U.S. Cl. .......................... 73/856; 73/860
(58) Field of Classification Search ............ 73/856, 73/796, 799, 810, 821, 826, 831, 846
    See application file for complete search history.

(56) References Cited

U.S. PATENT DOCUMENTS

| | | | | |
|---|---|---|---|---|
| 3,789,508 A | * | 2/1974 | Meline | 33/788 |
| 4,003,246 A | * | 1/1977 | Cain | 73/799 |
| 4,464,937 A | * | 8/1984 | Watts et al. | 73/772 |
| 5,638,206 A | * | 6/1997 | Sumiya et al. | 359/368 |
| 6,170,337 B1 | * | 1/2001 | Zeman | 73/783 |
| 2002/0017146 A1 | * | 2/2002 | Oliver | 73/856 |
| 2004/0144180 A1 | * | 7/2004 | Imamura | 73/796 |

* cited by examiner

*Primary Examiner*—Edward Lefkowitz
*Assistant Examiner*—Punam Patel
(74) *Attorney, Agent, or Firm*—MacMillan, Sobanski & Todd, LLC

(57) ABSTRACT

A fixture for measuring the elongation of a specimen includes a base. The base carries a fixture portion, and the fixture portion is provided with a surface adapted to receive a portion of the specimen.

7 Claims, 5 Drawing Sheets

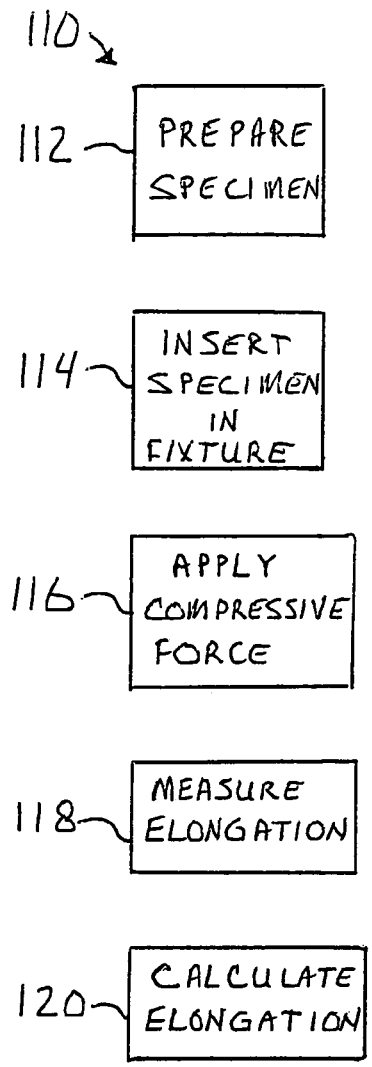
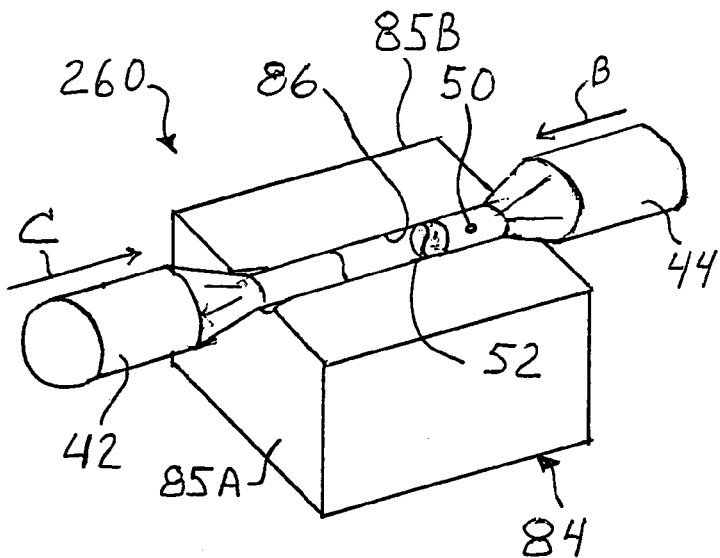
FIG. 9
FIG. 8

FIXTURE AND METHOD FOR MEASURING ELONGATION

BACKGROUND OF THE INVENTION

The present invention relates in general to a fixture and method for measuring elongation of a sample specimen. More specifically, this invention relates to an improved fixture and method for measuring elongation of a sample specimen.

It is known to measure the elongation of a sample specimen cut from a cast metal workpiece such as an automotive component. Such sample specimens are often cut and formed from varying locations within the workpiece to be tested. Elongation measurements of sample specimens cut from different locations in the workpieces are known to vary, resulting in inconsistent sample measurement data. Typically, such measurements of a sample specimen are taken with a caliper by an operator while the operator holds the specimen in his/her hand, causing further variation and inconsistency in the sample measurement data. Such a method of measuring elongation of a sample specimen thereby results in undesirable inconsistent elongation measurements. Thus, it would be desirable to provide a fixture and an improved method for measuring elongation of a sample specimen.

SUMMARY OF THE INVENTION

The present invention relates to a fixture for measuring the elongation of a specimen. The fixture includes a base. The base carries a fixture portion, and the fixture portion is provided with a surface adapted to receive a portion of the specimen.

Other advantages of this invention will become apparent to those skilled in the art from the following detailed description of the invention, when read in light of the accompanying drawings.

BRIEF DESCRIPTION OF THE DRAWINGS

FIG. 5 is a side elevational view of a second embodiment of a fixture for measuring the elongation of a sample specimen in accordance with this invention.

FIG. 6 is a top plan view of the fixture shown in FIG. 5.

FIG. 9 is a perspective view of a fourth embodiment of the fixture for measuring the elongation of a sample specimen in accordance with this invention.

DETAILED DESCRIPTION OF THE INVENTION

Figure 2:
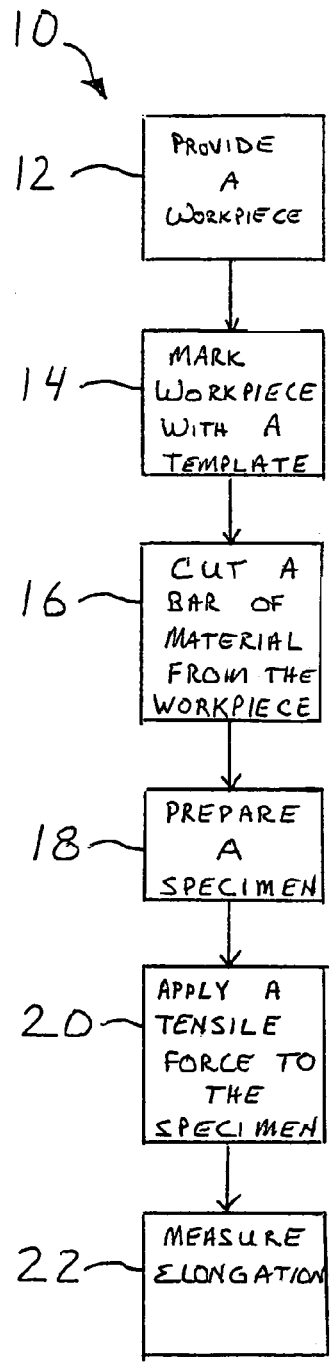
FIG. 2 is a flow chart of a method of measuring the elongation of a sample specimen in accordance with this invention.

Referring now to the drawings, there is illustrated in FIG. 2 a flow chart of a method, indicated generally at 10, for preparing a specimen or "tensile" bar for measurement of its elongation. The illustrated method is intended to illustrate one environment in which this invention may be practiced. Thus, the scope of this invention is not intended to be limited for use with the specific method for measuring elongation of a specimen 40 as illustrated in prior art FIG. 1, or to the measurement of elongation in general. On the contrary, as will become apparent below, this invention may be used in any desired environment for the purposes described below.

In a first step 12 of the illustrated method 10, a workpiece is provided. The workpiece may be a cast metal workpiece, such as a wheel knuckle for a vehicle, partially shown at 30 in FIG. 3. However, the workpiece 30 may be any suitable workpiece or object, the physical properties of which are to be measured. The workpiece 30 may be formed from a relatively lightweight metallic material, such as aluminum or alloys thereof. However, iron or any other desired metallic or non-metallic materials may be used to form the workpiece 30.

Figure 3:
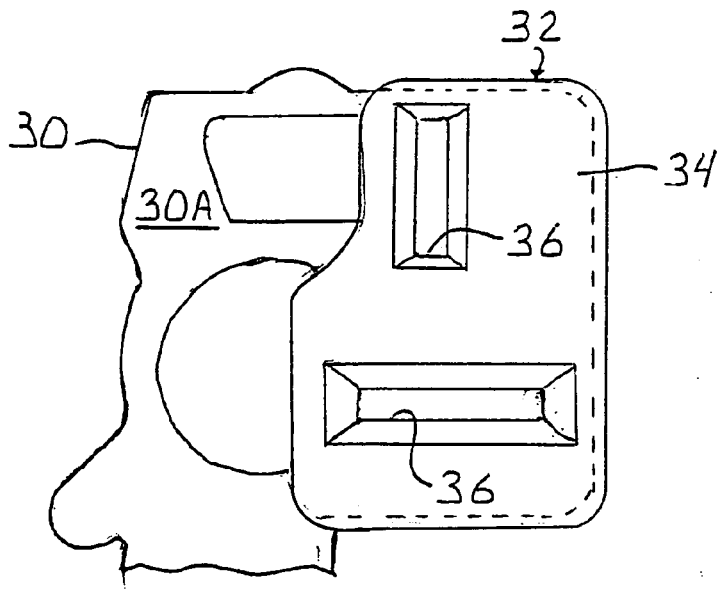
FIG. 3 a top plan view of a casting and a template for marking a bar of material in accordance with the method of FIG. 2.

In a second step 14 of the illustrated method 10, a specimen template, indicated generally at 32 in FIG. 3, is disposed on a surface 30A of the workpiece 30. In the illustrated embodiment, the specimen template 32 includes a body 34. In the illustrated embodiment, the body 34 has two substantially rectangularly shaped openings 36. The particular size, shape and/or configuration of the specimen template body 34 may be other than illustrated if so desired depending on the size and shape of the workpiece 30 upon which the template 32 is disposed. The template 32 may also include any desired number and/or shape of openings 36. In the embodiment illustrated in FIG. 3, the template 32 includes a workpiece-engaging surface (i.e., a downwardly facing surface in FIG. 2). The workpiece-engaging surface may be contoured or shaped to correspond to the shape of the surface 30A of the workpiece 30. If desired, the template 32 may be temporarily attached to the workpiece 30 with fasteners, such as threaded fasteners, or clamps. Such fasteners however, are not required.

In operation, during step 14, an operator disposes the template 32 on the surface 30A of the workpiece 30. The operator then uses a suitable marking device, such as a pencil or marking pen, to apply the shape of the opening(s) 36 onto the surface of the workpiece 30, thereby marking the portion of the workpiece 30 from which a bar of material (not shown) will be cut. The use of the template 32 ensures that each bar of material, from which a specimen 40 (described in detail below in connection with prior art FIG. 1) will be formed, is cut from the same portion of each workpiece. The template 32 may be formed from a relatively lightweight metallic material, such as aluminum, or alloys thereof. The template 32 may also be formed from plastic. However, any other desired metallic or non-metallic material may also be used to form the template 32.

The third step 16 of the illustrated method involves cutting one or more bars of material from the workpiece 30. Any desired method for cutting the bar(s) of material from a workpiece 30 may be used, such as using a saw. As is know in the art, the bar of material that is cut from the workpiece 30 is cut so as to have a size which is larger than the size of the particular specimen which is to be formed.

Figure 1:
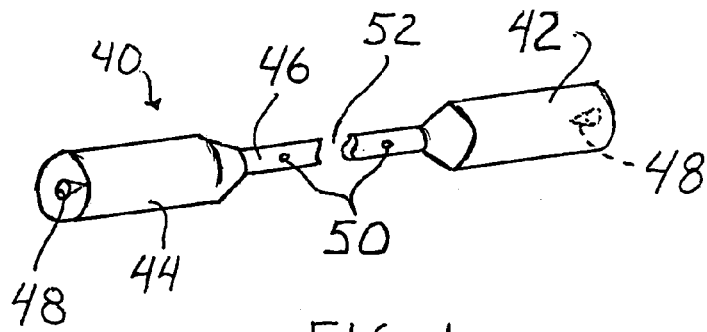
FIG. 1 is a perspective view of a prior art sample specimen.

In the fourth step 18 of the illustrated prior art method 10, the bar of material cut from the workpiece 30 is machined or otherwise formed into a desired shape to produce the specimen 40, shown in prior art FIG. 1.

As shown in prior art FIG. 1, the illustrated specimen 40 includes a substantially cylindrical first end portion 42, a substantially cylindrical second end portion 44, and a substantially cylindrical reduced diameter body or center section 46 extending between the first end portion 42 and the second end portion 44. However, the specimen 40 may have any other desired shape. The specimen 40 includes a hole 48 formed in an end surface of each of the first and second end portions 42 and 44. In the illustrated embodiment, the holes 48 are substantially conical in shape. However, the holes 48 may have any other desired shape. In the illustrated embodiment, the specimen 40 further includes two holes 50 formed in the center section 46. The holes 50 are formed having a desired shape by a suitable process, such as with a punch, at any known distance apart. In the illustrated embodiment, the holes 50 are formed 1.0+/−0.005 inch apart. However, the holes 50 may be formed at any known distance apart for purposes described below.

The fifth step 20 of the illustrated method 10 involves applying a tensile force to the specimen 40. To accomplish this, the first and second ends 42 and 44 of the specimen 40 may be disposed within a pair of grippers or jaws of a conventional tensile load machine (not shown). A tensile load or tensile force may be applied to at least one of the first and the second ends 42 and 44 of the specimen 40, until the specimen 40 breaks, thereby defining a break, and separating the first and second ends 42 and 44. Such a tensile load machine is conventional in the art, and illustrates one environment or apparatus in which the specimen 40 may be used. However, any apparatus which is operative to pull or apply a tensile force to the specimen 40, and detects and measures the applied tensile stress can be used.

In a sixth step 22 of the illustrated method 10, an operator reassembles the separated first and second ends 42 and 44 at the break (the break being illustrated by reference character 52 in prior art FIG. 1. In a conventional method of measuring elongation, the operator may then hold the reassembled specimen 40 in one hand, and measure the distance between the two holes 50. To accomplish this, the operator typically uses a known caliper (not shown) to measure the distance between the two holes 50. However, other hand held measuring instruments may be used. If desired, caliper extensions, such as centerline gages, can be added to the caliper jaws to extend the length of the jaws. The distance between the two holes 50 is then measured and compared to the known distance between the two holes 50 (i.e. 1.0+/−0.005 inch), as measured prior to the application of the tensile force during step 20. The difference between the known distance and the measured distance defines the elongation of the specimen 40. A method for measuring elongation of a specimen in accordance with the method of this invention will be described in detail below.

Figure 4:
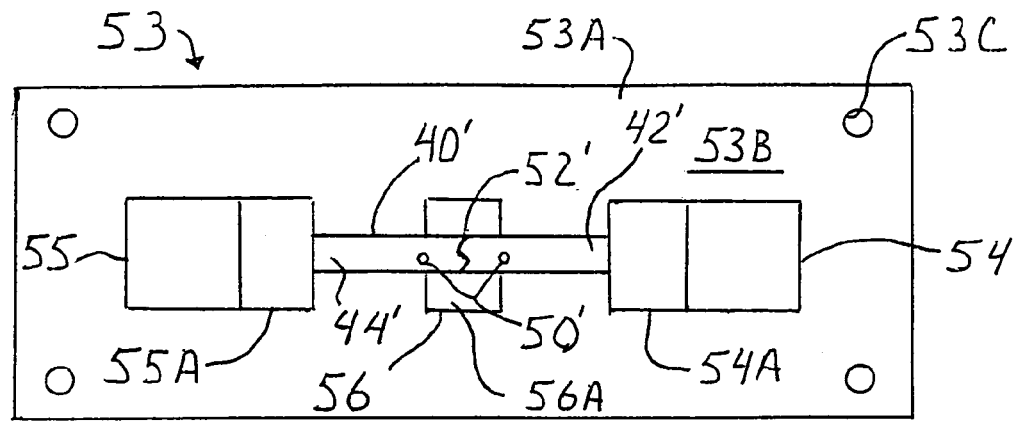
FIG. 4 is a schematic top plan view of a first embodiment of a fixture for measuring the elongation of a sample specimen in accordance with this invention.

Referring now to FIG. 4 and using like reference numbers to indicate corresponding parts, there is illustrated a schematic top plan view of a first embodiment of a fixture, indicated generally at 53, for measuring the elongation of a specimen 40' having a break 52', in accordance with the sixth step 22 of this invention. In this embodiment, the fixture 53 includes a body or base 53A having an upwardly facing surface 53B. The base 53A may include a plurality of mounting holes 53C for attaching the base 53A to an object, as will be described below.

In the illustrated embodiment, the fixture 53 includes a first fixture portion 54 that extends upwardly from the base 53A. The first fixture portion 54 may be attached to the base 53A by any desired means, such as threaded fasteners. Means for applying a compressive force 54A, the purpose of which will be described below, may be provided adjacent, or attached to, the first fixture portion 54. In the illustrated embodiment, the means for applying a compressive force 54A is adjacent an end of the first fixture portion 54, although such means may be provided at any suitable location.

The fixture 53 includes a second fixture portion 55 that extends upwardly from the base 53A, as shown in FIG. 4. The second fixture portion 55 may be attached to the base 53A by any desired means, such as threaded fasteners. Means for measuring the compressive force 55A, such as a load cell, may be provided adjacent, or attached to, the second fixture portion 55. In the illustrated embodiment, the means for measuring a compressive force 55A is adjacent an end of the second fixture portion 55, although such means may be provided at any suitable location.

The fixture 53 further includes a third fixture portion 56 that extends upwardly, as viewed in FIG. 4, generally intermediate the first fixture portion 54 and the second fixture portion 55. The third fixture portion 56 may be attached to the base 53A by any desired means, such as threaded fasteners. Alternately, the third fixture portion 54 may be movably attached to the base 53A such that the third fixture portion 54 is in a readily adjustable and/or sliding engagement with the base 53A. The third fixture portion 56 may include a specimen engaging surface 56A. If desired the specimen engaging surface 56A may be shaped to receive a center section, including the break 52', of the specimen 40'. However, the engaging surface 56A may have any other desired shape.

In operation, the specimen 40' may be disposed in the fixture 53. In the illustrated embodiment, the first end portion 42' and the second end portion 44' of the specimen 40' are disposed to engage the respective inner ends of the means for applying a compressive force 54A and the means for measuring the compressive force 55A. A compressive force may then be applied to the specimen 40' by the means for applying compressive force 54A. The compressive force may be applied until a desired level of compression is achieved.

After application of the compressive force, the distance between the two holes 50' may then be measured. The distance between the holes 50' may be measured by any desired method, such as with a caliper or with a microscope, as will be described in detail below. The distance between the two holes 50' may also be measured by any other suitable method. The measured distance between the two holes 50' may then be compared to the known distance between the two holes (i.e., 1.0+/−0.005 inch), as measured prior to the application of a tensile force. The difference between the known distance and the measured distance defines the elongation of the specimen 40'.

Referring now to FIGS. 5 and 6 and using like reference numbers to indicate corresponding parts, there are illustrated a side elevational view and a top plan view, respectively, of a second embodiment of a fixture, indicated generally at 60, for measuring the elongation of a specimen 40 in accordance with this invention. In the illustrated embodiment, the fixture 60 includes a body or base 62 having an upwardly facing surface 64 and an axis A1. The base 62 may include a plurality of mounting holes 66 for attaching the base 62 to an object, such as a microscope 88, as will be described below.

The fixtures 60 includes a first fixture portion 68 that extends upwardly, as viewed in FIG. 5, from the base 62, and has an inner end 68A and an outer end 68B. The first fixture portion 68 may be attached to the base 62 with fasteners such as the bolts 70 illustrated in FIG. 5. However, the first fixture portion 68 may be attached to the base 62 by any desired means. In the illustrated embodiment, a bore 68C is formed through the first fixture portion 68 and extends from the outer end 68B to the inner end 68A. If desired, a substantially cylindrical pin 68D may extend upwardly into the bore 68C.

In the illustrated embodiment, threads 71 are formed on an inner surface of the bore 68C. The threads 71 receive the external threads 72A of a threaded shaft 72 which may be disposed within the bore 68C at the outer end 68B of the first fixture portion 68. The shaft 72 may include a handle 72B, such as an adjustable torque handle, at an outer end thereof. Such an adjustable torque handle 72B may be provided to prevent over-tightening of the shaft 72. However, the adjustable torque handle 72B is not required, and any handle or device can be provided. Alternately, the shaft 72 may be rotated by hand. In the illustrated embodiment, a compressive force rod 74 is disposed within the bore 68C at the inner end 68A of the first fixture portion 68 and is attached to an inner end of the shaft 72. An inner end of the rod 74 defines a first specimen mounting surface 74A. In the illustrated embodiment, the first specimen mounting surface 74A is substantially conical in shape. However, the first specimen mounting surface 74A may have any desired shape. The rod 74 may be provided with a groove 74B having a stop surface 74C, as best shown in FIG. 5. In the illustrated embodiment, the pin 68D extends upwardly into sliding engagement with the groove 74B, to limit rotational and inward axial movement of the rod 74.

The fixture 60 includes a second fixture portion 76 that extends upwardly from the base 62, as viewed in FIG. 5, and has an inner end 76A and an outer end 76B. The second fixture portion 76 may be attached to the base 62 with fasteners such as the bolts 70 illustrated in FIG. 5. However, the second fixture portion 76 may be attached to the base 62 by any desired means. In the illustrated embodiment, a load cell 78 is attached to the inner end 76A of the second fixture portion 76. The illustrated load cell 78 is, for the most part, conventional in the art and will not be discussed in detail herein. The load cell 78 may be attached to the second fixture portion 76 with a fastener (not shown), such as a threaded fastener. However, the load cell 78 may be attached to the second fixture portion 76 by any desired means. A load monitor 78A may be attached to the load cell 78 by a flexible electric cable 78B. In the illustrated embodiment, the load monitor 78A is a hand held load monitor. However, any suitable load monitor 78A may be used.

In the illustrated embodiment, a specimen mount 80 may extend axially from an inner end of the load cell 78. An inner end of the mount 80 defines a second specimen mounting surface 80A. In the illustrated embodiment, the second specimen mounting surface 80A is substantially conical in shape. However, the second specimen mounting surface 80A may have any desired shape. The mount 80 may be attached to the load cell 78 with a fastener (not shown), such as a threaded fastener. However, the mount 80 may be attached to the load cell 78 by any desired means. In the illustrated embodiment, an adjustable stop 82 extends inwardly from the inner end 76A of the second fixture portion 76. The adjustable stop 82 may include a threaded rod 82A and a nut 82B.

The fixture 60 includes a third fixture portion 84 that extends upwardly, as viewed in FIG. 5, intermediate the first fixture portion 68 and the second fixture portion 76. The third fixture portion 84 includes a body 84A and a mounting portion 84B. In the illustrated embodiment, the body 84A includes a first or side surface 85A and a second or rear surface 85B. The mounting portion 84B may be attached to the base 62 through holes 84C with fasteners such as the bolts 70 illustrated in FIG. 5. However, the mounting portion 84B may be attached to the base 62 by any desired means. The third fixture portion 84 may include a specimen engaging surface 86 shaped to receive the center section 46 of the specimen 40. In the illustrated embodiment, the engaging surface 86 is a groove formed in an upwardly facing surface of the third fixture portion 84. However, the engaging surface 86 may have any desired shape.

In the illustrated embodiment, the body 84A is preferably disposed in an adjustable sliding engagement with the surface 64 of the base 62. The body 84A is further disposed such that the rear surface 85B is in an adjustable sliding engagement with the mounting portion 84B. In operation, an operator may position the body 84A to a desired position by moving the adjustable stop 82 inwardly or outwardly relative to the body 84A, and moving the body 84A such that the side surface 85A engages the rod 82A. The ability to slidably move the body 84A relative to the base 62 allows an operator to position the body 84A to any desired position relative to the base 62. It will be understood that the engaging surface 86 of the third fixture portion body 84A may have any desired shape or configuration, thereby allowing the fixture 60 to be used to measure the elongation of different sizes and shapes of specimens.

Figure 11:
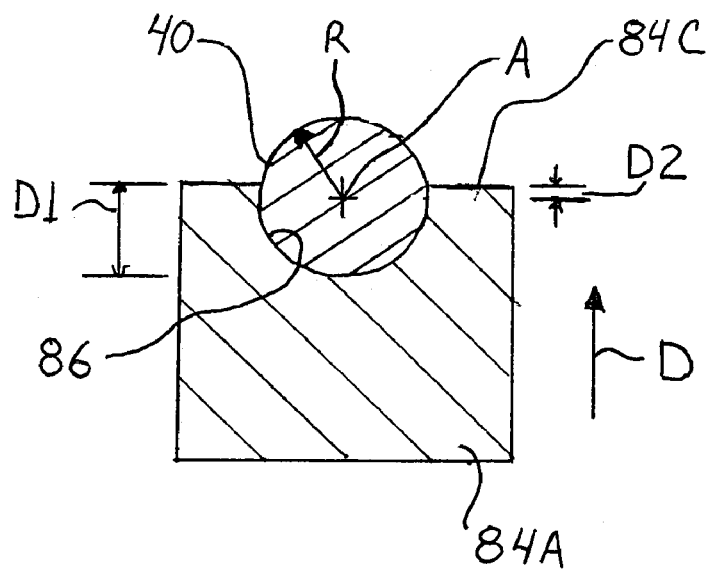
FIG. 11 is an enlarged sectional view of a portion of the fixture taken along line 11-11 of FIG. 6.

As best shown in FIG. 11, the body 84A includes the groove 86 and an upper surface 84C. In the illustrated embodiment, specimen 40 is shown disposed within the groove 86 and includes an axis A2 and a radius R. The illustrated groove 86 has a depth D1 as measured from the upper surface 84C to the lowest portion of the groove 86. In the illustrated embodiment, the depth D1 is greater than the radius R. The groove 86 may be formed such that a distance D2, as measured from the surface 84C to the axis A, is within the range of about 5 percent of the radius R. However, the distance D2 may be any desired distance.

FIG. 9 is a perspective view of another embodiment of a fixture, indicated generally at 260, for measuring the elongation of the specimen 40 in accordance with this invention. In the illustrated embodiment, structure and function of the fixture 260 is otherwise identical to the body 84A of the third fixture portion 84, and will not be further described herein.

In operation, the first and second ends 42 and 44 of the separated specimen 40 may be inserted longitudinally into the groove 86 in the direction of the arrows B and C, respectively, as best shown in FIG. 9. Because the depth D1 is greater than the radius R, when the specimen 40 is inserted into the groove 86, as shown in the embodiment illustrated in FIG. 11, the specimen 40 resists or is prevented from moving outwardly, such as in the direction of the arrow D, of the groove 86 (upwardly when viewed in FIG. 11). If desired, an operator may apply a compressive force on the first and second end portions 42 and 44 to reassemble the specimen 40 at the break 52. The operator may then measure the distance between the holes 50 by any desired method, such as with a caliper.

The first, second, and third fixture portions 68, 76, and 84 may be formed from a metallic material, such as steel, aluminum, or alloys thereof. However, any other desired metallic or non-metallic material may be used to form the first, second, and third fixture portions 68, 76, and 84.

Figure 7:
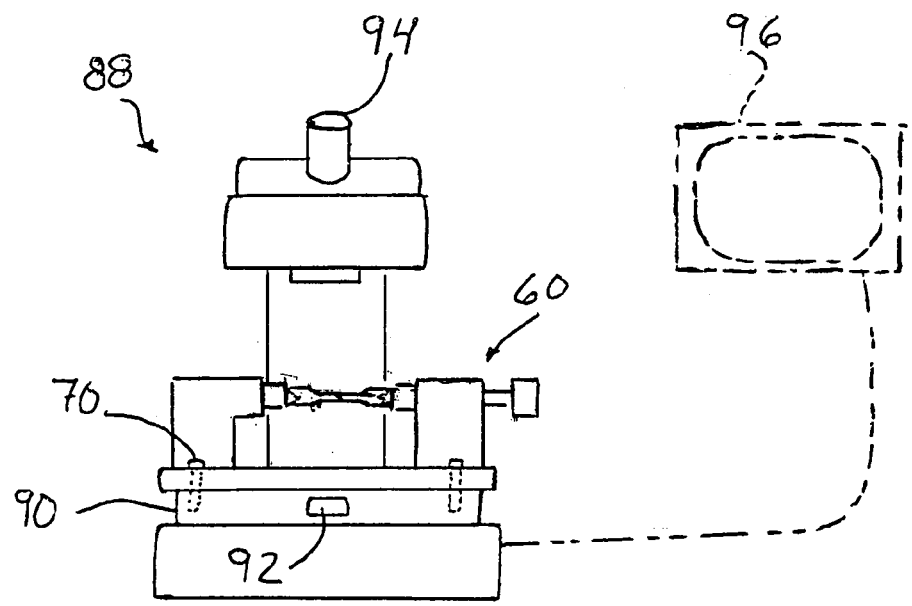
FIG. 7 is a side elevational view of a third embodiment of a fixture for measuring the elongation of a sample specimen in accordance with this invention.

If desired, as shown in the embodiment illustrated in FIG. 7, the fixture 60 (illustrated schematically) may be mounted to a microscope 88. The illustrated microscope 88 includes a mounting plate 90. The fixture 60 may be mounted to the microscope mounting plate 90 with fasteners such as the bolts 70. However, the fixture 60 may be attached to the mounting plate 90 by any desired means. If desired, a movement controller 92 may be provided to allow an operator to move the mounting plate 90, and thereby move the attached fixture 60, relative to the microscope 88. The illustrated microscope 88 includes an eyepiece 94, although an eyepiece is not required. The microscope 88 may further include a digital display (not shown) within the microscope 88 and viewable through the eyepiece 94, for displaying a measured distance between the two holes 50. If desired, the microscope 88 may include a display screen 96, illustrated in phantom in FIG. 7, for displaying the measured distance between the two holes 50. However, such a display screen 96 is not required. The display screen 96 may be any desired type of display screen, such as a computer screen or other video monitor. It will be understood that the fixture 60 may be used with any desired apparatus for measuring a distance, such as an apparatus for measuring a distance in one or more directions, such as x, y, and z directions.

Figure 8:
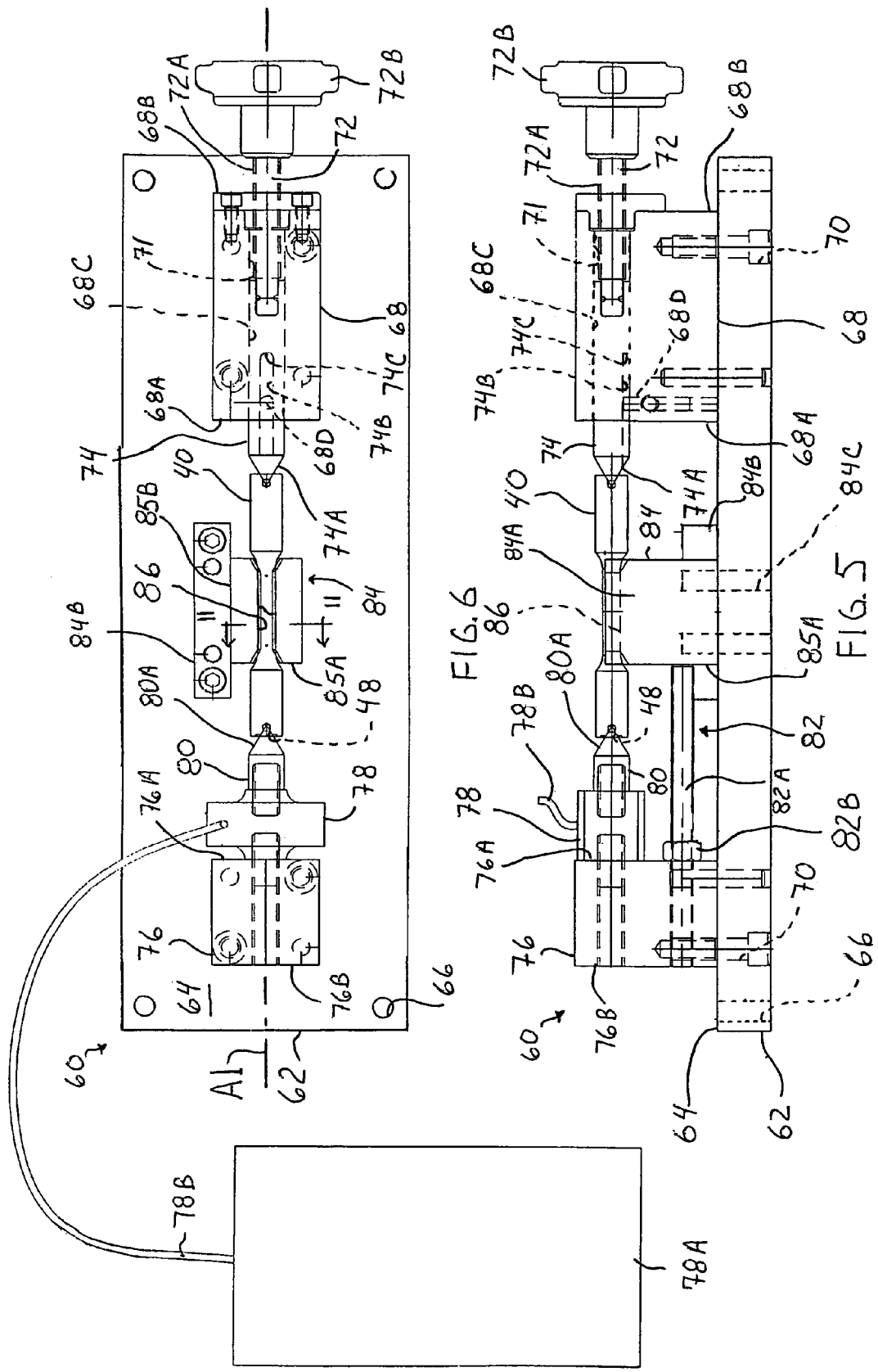
FIG. 8 is a flow chart of a method of measuring the elongation of a sample specimen in accordance with this invention.

Referring now to FIG. 8, a flow chart of a method for measuring elongation of a specimen in accordance with the method of this invention is indicated generally at 110. In a first step 112 of the illustrated method 110, specimen 40 is prepared as described above. As also described above, a tensile force is applied to the specimen 40 until the specimen 40 breaks to define the break 52, and separates the first and second ends 42 and 44, as best shown in prior art FIG. 3.

In a second step 114 of the illustrated method 110, the separated first end 42 (not illustrated in FIG. 9) and the second end 44 may be inserted longitudinally into the groove 86 in the direction of the arrows B and C, respectively, as best shown in FIG. 9, thereby reassembling the specimen at the break 52. In the embodiment illustrated in FIGS. 4 through 6, the center section 46 of the reassembled specimen 40 is disposed in the groove 86 of the third fixture portion 84. The first end portion 42 and the second end portion 44 of the specimen 40 may then be disposed such that the first specimen mounting surface 74A and the second specimen mounting surface 80A, respectively, are disposed within the substantially conical first holes 48.

In a third step 116 of the illustrated method 110, a compressive force is applied to the specimen 40 by the means for applying compressive force, such as by rotating the shaft 72 with the adjustable torque handle 72B, thereby causing the rod 74 to move inwardly against the specimen 40. The compressive force may be applied until a desired level of compression is achieved, as may be indicated on the load monitor 78A, as best shown in FIG. 6. In the illustrated embodiment, a compressive force is applied in accordance with a desired specimen test standard, such as prescribed by ASTM test standard B557. For example, a compressive force of about 2000 lbs./in$^2$ of a cross-section of the specimen 40 may be applied to the first and/or second end portions 42 and 44 of the specimen 40 prior to measuring the distance between the two holes 50. In the prior art method as described above, when the specimen 40 is reassembled by hand in step 22. In such a reassembly step, the operator cannot apply a uniform or consistent force, or may apply substantially no force, to the first and second end portions 42 and 44 of the specimen 40.

In a fourth step 118 of the illustrated method 110, the distance between the two holes 50 may then be measured. The distance between the two holes 50 may be measured by any desired method, such as with a caliper. Alternately, the distance between the two holes 50 may be measured with the microscope 88, as best shown in FIG. 7. However, the distance between the two holes 50 may be measured by any other suitable method.

In a fifth step 120 of the illustrated method 110, the measured distance between the two holes 50 may then be compared to the known distance between the two holes (i.e., 1.0+/−0.005 inch), as measured prior to the application of a tensile force. The difference between the known distance and the measured distance defines the elongation of the specimen 40.

Figure 10:
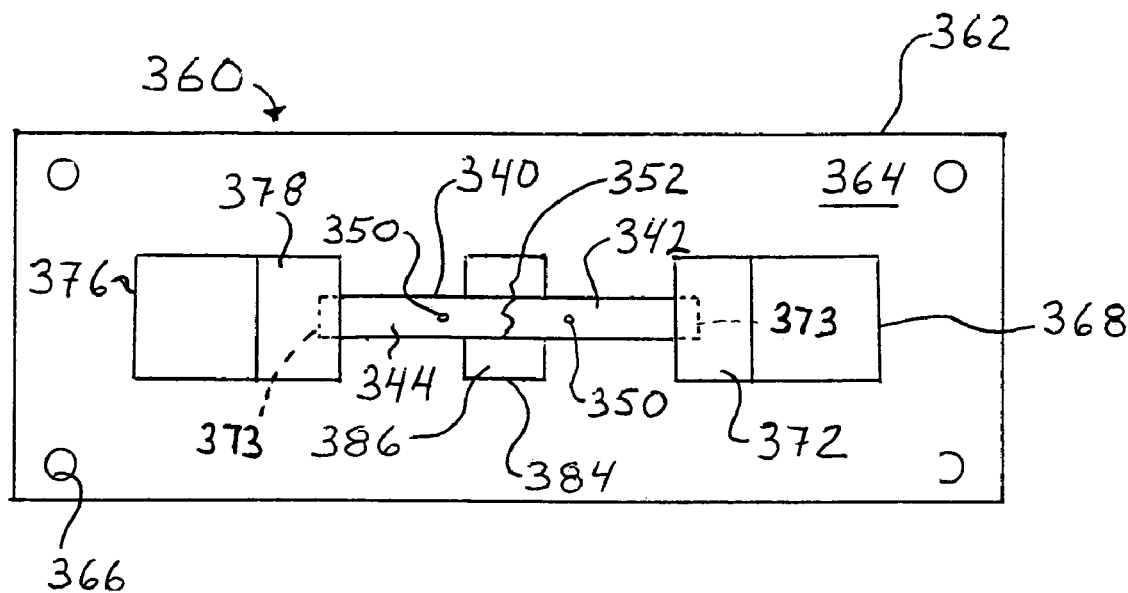
FIG. 10 is a top plan view of a firth embodiment of a fixture for measuring the elongation of a sample specimen in accordance with this invention.

FIG. 10 is schematic top plan view of another embodiment of a fixture, indicated generally at 360, for measuring the elongation of a specimen 340 having a break 352, in accordance with this invention. In the illustrated embodiment, the fixture 360 includes a base 362 having an upwardly facing surface 364. The base 362 may include a plurality of mounting holes 366 for attaching the base 362 to an object, such as the microscope 88.

In the illustrated embodiment, a first fixture portion 368 extends upwardly from the base 362. The first fixture portion 368 may be attached to the base 362 by any desired means, such as threaded fasteners. Means for applying a compressive force and a tensile force 372 may be provided adjacent, or attached to, the first fixture portion 368. In the illustrated embodiment, the means for applying a compressive force and a tensile force 372 is adjacent an inner end of the first fixture portion 368, although such means may be provided at any suitable location.

A second fixture portion 376 may extend upwardly from the base 362, as shown in FIG. 10. The second fixture portion 376 may be attached to the base 362 by any desired means, such as threaded fasteners. Means for measuring the compressive force and the tensile force 378, may be provided adjacent, or attached to, the second fixture portion 376. In the illustrated embodiment, the means for measuring the compressive force and the tensile force 378 is adjacent an inner end of the second fixture portion 376, although such means may be provided at any suitable location.

A third fixture portion 384 may extend upwardly, as viewed in FIG. 10, intermediate the first fixture portion 368 and the second fixture portion 376. The third fixture portion 384 may be attached to the base 362 by any desired means, such as threaded fasteners. Alternately, the third fixture portion 384 may be movably mounted such that the third fixture portion 384 is in a sliding engagement with the surface 364 of the base 362. The third fixture portion 384 may include a specimen engaging surface 386. If desired, the specimen engaging surface 386 may be shaped to receive a center section, including the break 352, of the specimen 340. However, the engaging surface 386 may have any desired shape.

In operation, the specimen 340 may be disposed in the fixture 360. In the illustrated embodiment, a first end portion 342 and a second end portion 344 of the specimen 340 are disposed so as to engage, such as within grippers or jaws 373, the respective ends of a combination means for applying a compressive and a tensile force 372 and a combination means for measuring the compressive and the tensile force 378.

A tensile force may be applied to at least one of the first and the second end portions 342 and 344 of the specimen 340 by the means 372 until the specimen 340 breaks, thereby defining the break 352, and separating the first and second ends 342 and 344.

A compressive force may then be applied to the specimen 340 by the means 372, thereby reassembling the specimen 340 at the break 352. The compressive force may be applied until a desired level of compression is achieved, as described above.

After application of the compressive force, the distance between the two holes 350 may then be measured. The distance between the holes 350 may be measured by any desired method, such as with a caliper or with a microscope, as described above. The distance between the two holes 350 may also be measured by any other suitable method. The measured distance between the two holes 350 may then be compared to the known distance between the two holes (i.e., 1.0+/−0.005 inch), as measured prior to the application of the tensile force. The difference between the known distance and the measured distance defines the elongation of the specimen 340.

The principle and mode of operation of this invention have been described in its various embodiments. However, it should be noted that this invention may be practiced otherwise than as specifically illustrated and described without departing from its scope.

What is claimed is:

1. A method for measuring elongation of a pre-elongated specimen, the method comprising the steps in the order of:
    a. providing a specimen fixture having a base and a fixture portion carried by the base, the fixture portion provided with a surface adapted to receive a portion of a specimen, wherein the fixture portion is an intermediate fixture portion and wherein a first fixture portion is disposed near a first side of the intermediate fixture portion and a second fixture portion is disposed near an opposite second side of the intermediate fixture, wherein one of the first and second fixture portions includes a compressive force applying means, and further including a means for measuring an applied compressive force applied by the compressive force applying means;
    b. providing the pre-elongated specimen, wherein the specimen includes a break separating a first end portion of the pre-elongated specimen and a second end portion of the pre-elongated specimen;
    c. disposing the pre-elongated specimen in the fixture; and
    d. measuring the elongation of the pre-elongated specimen.

2. The method according to claim 1 wherein the surface includes a groove formed therein.

3. The method according to claim 1 wherein the other one of the first and second fixture portions includes a load cell.

4. The method according to claim 3 further including a load monitor connected to the load cell.

5. The method according to claim 1 wherein the step of measuring the elongation of the pre-elongated specimen includes providing an elongation measuring device.

6. The method according to claim 5 wherein the elongation measuring device is a caliper.

7. The method according to claim 5 wherein the elongation measuring device is a microscope.

\* \* \* \* \*